United States Patent [19]

Ondetti et al.

[11] 4,241,076
[45] Dec. 23, 1980

[54] HALOGENATED SUBSTITUTED MERCAPTOACYLAMINO ACIDS

[75] Inventors: Miguel A. Ondetti, Princeton; Peter W. Sprague, Pennington, both of N.J.

[73] Assignee: E. R. Squibb & Sons, Inc., Princeton, N.J.

[21] Appl. No.: 37,255

[22] Filed: May 9, 1979

Related U.S. Application Data

[63] Continuation-in-part of Ser. No. 939,148, Sep. 1, 1978, abandoned, which is a continuation-in-part of Ser. No. 879,032, Feb. 21, 1978, abandoned.

[51] Int. Cl.$^3$ .................. A61K 31/40; C07D 207/16
[52] U.S. Cl. .................. 424/274; 260/326.2; 260/326.25; 260/326.43
[58] Field of Search .......... 260/326.2, 326.25, 326.43; 424/274

[56] References Cited

U.S. PATENT DOCUMENTS

| | | | |
|---|---|---|---|
| 4,046,889 | 9/1977 | Ondetti et al. | 260/326.2 |
| 4,052,511 | 10/1977 | Cushman et al. | 260/326.2 |
| 4,070,361 | 1/1978 | Petrillo, Jr. | 260/326.2 |
| 4,086,338 | 4/1978 | Cushman et al. | 260/326.2 |
| 4,091,024 | 5/1978 | Ondetti | 260/326.2 |
| 4,105,776 | 8/1978 | Ondetti et al. | 260/326.2 |
| 4,108,886 | 8/1978 | Ondetti | 260/326.2 |
| 4,113,715 | 9/1978 | Ondetti et al. | 260/326.2 |
| 4,116,962 | 9/1978 | Ondetti et al. | 260/326.2 |
| 4,127,729 | 11/1978 | Ondetti | 260/326.2 |
| 4,128,721 | 12/1978 | Ondetti | 260/326.2 |
| 4,129,571 | 12/1978 | Ondetti et al. | 260/326.2 |
| 4,140,864 | 2/1979 | Ondetti et al. | 260/326.2 |
| 4,154,736 | 5/1979 | Ondetti | 260/326.2 |
| 4,154,935 | 5/1979 | Ondetti et al. | 260/326.2 |
| 4,154,960 | 5/1979 | Ondetti et al. | 260/326.2 |
| 4,156,789 | 5/1979 | Ondetti et al. | 260/326.2 |
| 4,198,515 | 4/1980 | Ondetti et al. | 260/326.2 |

OTHER PUBLICATIONS

Yale; J. Med. and Pharm. Chem. vol. 1, No. 2 (1959), pp. 121-133.
Shiroto et al.; J. Med. Chem., vol. 20, pp. 1176-1181, (1977).

*Primary Examiner*—Mary C. Lee
*Attorney, Agent, or Firm*—Lawrence S. Levinson; Stephen B. Davis

[57] ABSTRACT

New halogen substituted mercaptoacylamino acids which have the general formula

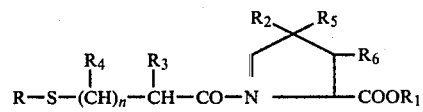

and basic salts thereof are useful as hypotensive agents.

38 Claims, No Drawings

HALOGENATED SUBSTITUTED MERCAPTOACYLAMINO ACIDS

RELATED APPLICATIONS

This application is a continuation-in-part of application Ser. No. 939,148, filed Sept. 1, 1978, now abandoned, which is a continuation-in-part of application Ser. No. 879,032, filed February 21, 1978, now abandoned.

Turk et al. in application Ser. No. 12,618, filed Feb. 16, 1979, now abandoned, disclose an improved process for preparing certain intermediates in 879,032 and 939,148.

BACKGROUND OF THE INVENTION

Ondetti et al. in U.S. Pat. Nos. 4,046,889 and 4,105,776 disclose compounds which are useful as inhibitors of angiotensin converting enzyme and can be utilized to reduce blood pressure. Among the compounds disclosed by Ondetti et al. are L-proline derivatives of the formula

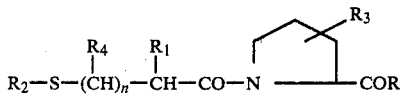

wherein n can be zero or one; R can be hydroxy; $R_1$ and $R_4$ can be hydrogen or lower alkyl; $R_2$ can be hydrogen, lower alkanoyl, or benzoyl; and $R_3$ can be hydrogen, hydroxy, or lower alkyl.

SUMMARY OF THE INVENTION

This invention relates to new halogenated compounds which have the general formula

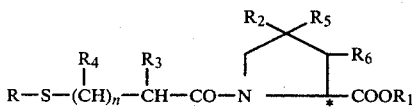

wherein
R is hydrogen, lower alkanoyl,

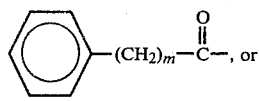

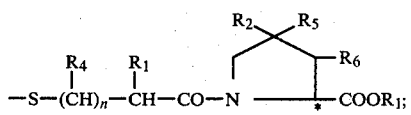

m is zero, one or two; preferably zero;
$R_1$ is hydrogen or lower alkyl;
$R_2$, $R_5$ and $R_6$ each is hydrogen or halogen;
$R_3$ is hydrogen, lower alkyl, halogen or trifluoromethyl provided that when n is zero $R_3$ is other than halogen;
$R_4$ is hydrogen, lower alkyl or trifluoromethyl;
n is zero or one; and the further proviso that at least one of $R_2$, $R_3$, $R_4$, $R_5$ and $R_6$ as defined above is a halogen or trifluoromethyl and that only $R_2$ and $R_5$ can both be halogen in the same compound and the two halogens are preferably the same.

DETAILED DESCRIPTION OF THE INVENTION

The invention in its broadest aspects relates to halogenated derivatives of mercaptoacyl prolines having formula I above.

Two preferential groups of compounds within formula I are those with the following formulas:

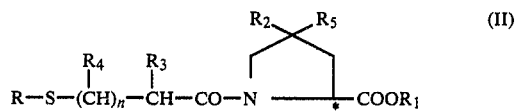

wherein
R is hydrogen, lower alkanoyl or

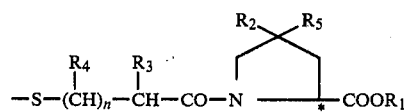

$R_1$ is hydrogen or lower alkyl;
$R_2$ and $R_5$ each is hydrogen or halogen provided that when $R_2$ and $R_5$ are both halogen the two halogens are the same;
$R_3$ and $R_4$ each is hydrogen or trifluoromethyl, one being hydrogen and the other trifluoromethyl; and n is zero or one;

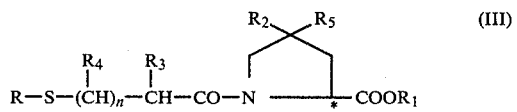

wherein
R and $R_1$ have the same meaning as defined above for formula II;
$R_2$ and $R_5$ each is hydrogen or halogen provided that when $R_2$ and $R_5$ are both halogen the two halogens are the same;
$R_3$ is hydrogen, halogen or lower alkyl,
$R_3$ being halogen when both $R_2$ and $R_5$ are hydrogen, $R_3$ being other than halogen when $R_2$ or $R_5$ is halogen;
$R_4$ is hydrogen; and
n is zero or one provided that n is one when $R_3$ is halogen; and basic salts of said compounds of formula II and III, respectively.

Thus in the case of formula II, when n is 0 and $R_2$ and $R_5$ are both hydrogen, $R_3$ is trifluoromethyl. When n is 1, either $R_3$ or $R_4$ is trifluoromethyl and the other is hydrogen. That is to say there is one trifluoromethyl group in the acyl side chain of the molecule. It is on the carbon α to the carbonyl group ($R_3$=CF$_3$) when n is 0. It is on either the carbon α to the carbonyl group ($R_3$=CF$_3$, $R_4$=H) or on the carbon β to the carbonyl group ($R_3$=H, $R_4$=CF$_3$) when n is 1, the other of the pair of symbols ($R_3$, $R_4$) is then hydrogen. When either $R_3$ or $R_4$ is trifluoromethyl, $R_2$ and $R_5$ each is hydrogen or halogen.

In the case of formula III, preferably one or both of $R_2$ and $R_5$ are halogen and $R_3$ and $R_4$ each is hydrogen or lower alkyl, or both $R_2$ and $R_5$ are hydrogen, $R_3$ is halogen, preferably chlorine or bromine, and $R_4$ is hydrogen.

Preferred as active final products are those compounds of formula I wherein R is hydrogen; $R_1$ is hydrogen; $R_2$ and $R_5$ each is hydrogen or halogen, especially hydrogen, chlorine, or fluorine; $R_3$ and $R_4$ each is hydrogen, trifluoromethyl or lower alkyl, especially hydrogen, trifluoromethyl, or methyl, one of $R_3$ or $R_4$ being trifluoromethyl and the other hydrogen when $R_2$, $R_5$, and $R_6$ are all hydrogen; and n is zero or one, especially one. Also preferred as final products and intermediates are the above defined compounds wherein R is acetyl.

The L-configuration for the proline is especially preferred.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The $C_1$–$C_4$ members, especially $C_1$ and $C_2$ members, are preferred.

The lower alkanoyl groups are those having the acyl radicals of the lower ($C_2$–$C_7$) fatty acids, for example, acetyl, propionyl, butyryl and the like. Similarly, those lower alkanoyl groups having up to four carbons, and especially acetyl, are preferred.

The halogens are the four common halogens, chlorine, bromine and fluorine being preferred. One or two halogens can be present on the pyrrolidine ring. A single halogen can be on either the carbon in the 3-position or the carbon in the 4-position. Two halogens can be present in the 4-position and preferably they are the same. Fluorine and chlorine are the preferred halogen substituents on this ring, especially one or two fluorine atoms in the 4-position.

The products of formula I can be produced by various methods of synthesis.

In general, these compounds can be synthesized by coupling the acid of the formula

to the amino acid of the formula

by any method which can be used to form amide bonds. See, for example, "Methoden der Organischen Chemie" (Houben-Weyl) part I, p. 376 et seq., part III, p. 1 et seq. (1974).

The acids of formula IV, when n is 1 can be obtained by the addition of a thioacid R—SH to a suitably substituted acrylic acid. As a temporary protection of the mercapto group in compounds of formula IV, R can be a p-methoxybenzyl group. This group is then removed with trifluoroacetic acid and mercuric acetate. The acids of formula IV, when n is 0, are obtained by a displacement reaction using a thioacid R—SH and a 2-halo acid.

According to one method, preferred when n is 0, an acid of formula V is coupled with a haloalkanoic acid of the formula

wherein X is halogen, preferably chlorine or bromine, by one of the known procedures in which the acid VI is activated, prior to reaction with the acid V, involving formation of a mixed anhydride, symmetrical anhydride, acid chloride, active ester, or use of Woodward reagent K, EEDQ (N-ethoxycarbonyl-2-ethoxy-1,2-dihydroquinoline) or the like.

The product of this reaction is a compound of the formula

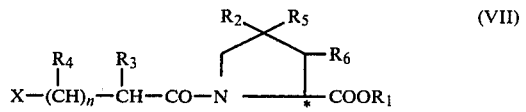

This product is subjected to a displacement reaction with the anion of a thioacid of the formula $$R_7\text{—CO—SH} \qquad \text{(VIII)}$$

wherein $R_7$ is lower alkyl or

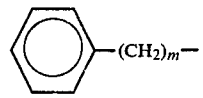

yielding a product of the formula

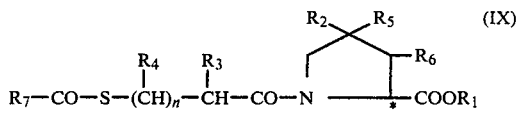

which can then be converted to the product

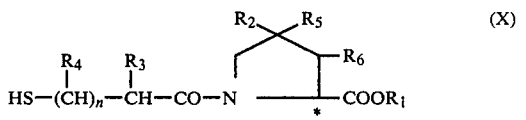

by conventional alkaline hydrolysis or by ammonolysis. When $R_1$ is an ester group (i.e., $R_1$ is lower alkyl, obtained when an ester of the starting acid V is used), the ester group can be removed by conventional techniques. For example, when $R_1$ is tert-butoxy or tert-amyloxy, treatment of the ester of formula IX or X with trifluoroacetic acid and anisole will give the corresponding free acid. When other alkoxy groups are present alkaline hydrolysis will yield the corresponding acid.

When an acid of formula V is used as starting material, or the final product is obtained as the free carboxylic acid, this acid can be converted to its ester, for example, by esterification with a diazoalkane, like diazomethane, 1-alkyl-3-p-tolyltriazene, like 1-n-butyl-3-p-tolyltriazene or the like.

According to another variation, an ester, preferably the methyl or t-butyl ester, of formula V, in an anhydrous medium such as dichloromethane, tetrahydrofuran, dioxane or the like, is treated with an acylthioalkanoic acid of the formula

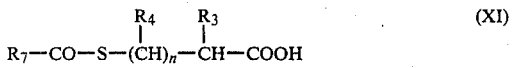 (XI)

in the presence of dicyclohexylcarbodiimide, N,N′-carbonylbisimidazole, ethoxyacetylene, diphenylphosphoryl azide or similar coupling agents at a temperature in the range of about 0° to 10° C. The ester group can then be removed, for example, by treatment with trifluoroacetic acid and anisole at about room temperature to yield the free acid ($R_1=H$).

A variation, preferred when n is 1, $R_4$ is $CF_3$ and $R_3$ is H, is to react a thioacid of formula VIII with an acrylic acid derivative of the formula

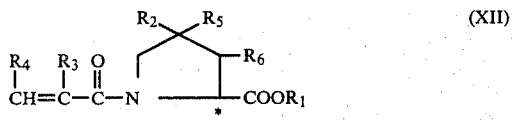 (XII)

instead of with the compound of formula VII, and then continue as described above. The compounds of formula XII are obtained from 3-trifluoromethylacrylic acid and an ester of formula V by the method described in Example 14 below.

Compounds of formula I wherein R is

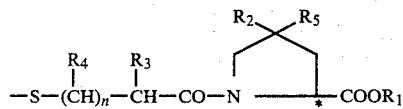

are produced by direct oxidation of a compound of formula I in which R is hydrogen, e.g., with iodine, to obtain the symmetrical bis compound.

Halogenated prolines of formula V which are used as starting materials can be produced by methods known in the art, e.g., Biochemistry 4, 2509 (1965), Aust. J. Chem. 20, 1493 (1967), J. Amer. Chem. Soc. 86, 4709 (1964), J. Med. Chem. 20,1176 (1977). An improved process for preparing the reactants of formula V when $R_2$ and $R_5$ are both fluorine and $R_6$ is hydrogen is disclosed by Turk et al. in application Ser. No. 12,618 filed Feb. 16, 1979 referred to above.

The asterisk in formula I and in some of the other formulas indicates an asymmetric center which is present in the proline ring. As stated above, the proline is preferably in the L-configuration. Of course, an additional asymmetric center can be present in the proline ring depending upon the substituents $R_2$, $R_5$ and $R_6$ and in the mercapto sidechain depending upon the substituents $R_3$ and $R_4$. The products of formula I accordingly exist in stereoisomeric forms or in racemic mixtures thereof. All of these are within the scope of the invention. The above described synthesis can utilize the racemate or one of the enantiomers as starting material. When the racemic starting material is used in the synthetic procedure, the stereoisomers obtained in the product can be separated by conventional chromatographic or fractional crystallization methods.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salts, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product.

The salts are formed in conventional manner by reacting the free acid form of the product with one or more equivalents of the appropriate base providing the desired salt ion, in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention are useful as hypotensive agents. They inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen → (renin) → angiotensin I → (ACE) → angiotensin II sequence by inhibiting angiotensin converting enzyme and reducing or eliminating the formation of the pressor substance angiotensin II. Thus by the administration of a composition containing one or a combination of compounds of formula I or a physiologically acceptable salt thereof, angiotensin dependent hypertension in the species of mammal suffering thereform is alleviated. A single dose, or preferably two to four divided daily doses, provided on a basis of about 0.1 to 100 mg. per kilogram per day, preferably about 1 to 50 mg. per kilogram per day, is appropriate to reduce blood pressure as indicated in the animal model experiments described by S. L. Engel, T. R. Schaeffer, M. H. Waugh and B. Rubin, Proc. Soc. Exp. Biol. Med. 143 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate or microcrystalline cellulose; a disintegrating agent such as corn starch, potato starch, alginic acid and the like, a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc.

The following examples are illustrative of the invention and constitute especially preferred embodiments. All temperatures are in degrees Celsius.

EXAMPLE 1

3-Acetylthio-2-trifluoromethylpropanoic acid

A mixture of thiolacetic acid (50 g.) and 2-(trifluoromethyl)acrylic acid [M. W. Buxton, et al. J. Chem. Soc., 366 (1954)] (66 g.) is heated on the steam bath for one hour and then stored at room temperature for eighteen hours. The reaction mixture is distilled in vacuo to give 3-acetylthio-2-trifluoromethylpropanoic acid.

EXAMPLE 2

1-(3-Acetylthio-2-trifluoromethylpropanoyl)-L-proline tert-butyl ester

L-proline tert-butyl ester (5.1 g.) is dissolved in dichloromethane (40 mg.) and the solution is stirred and chilled in an ice bath. Dicyclohexylcarbodiimide (6.q g.) dissolved in dichloromethane (15 ml.) is added followed immediately by a solution of 3-acetylthio-2-trifluoromethylpropanoic acid (6.5 g.) in dichloromethane (5 ml.). After fifteen minutes stirring in the ice bath and sixteen hours at room temperature, the precipitate formed is filtered off and the filtrate is concentrated to dryness in vacuo. The residue is dissolved in ethyl acetate and washed neutral. The organic phase is dried over magnesium sulfate and concentrated to dryness in vacuo to give 1-(3-acetylthio-2-trifluoromethylpropanoyl)-L-proline tert-butyl ester.

EXAMPLE 3

1-(3-Acetylthio-2-trifluoromethylpropanoyl)-L-proline 1-(3-Acetylthio-2-trifluoromethylpropanoyl)-L-proline tert-butyl ester (8 g.) is dissolved in a mixture of anisole (55 ml.) and trifluoroacetic acid (110 ml.). After one hour storage at room temperature the solvent is removed in vacuo and the residue is precipitated several times from etherhexane to give 1-(3-acetylthio-2-trifluoromethylpropanoyl)-L-proline.

EXAMPLE 4

1-(3-Mercapto-2-trifluoromethylpropanoyl)-L-proline 1-(3-Acetylthio-2-trifluoromethylpropanoyl)-L-proline (4 g.) is dissolved in a mixture of water (8 ml.) and concentrated ammonia (8 ml.) under a blanket of nitrogen. After twenty-five minutes stirring at room temperature, the reaction mixture is chilled, acidified and extracted with ethyl acetate. The organic layer is concentrated to dryness in vacuo to yield 1-(3-mercapto-2-trifluoromethylpropanoyl)-L-proline.

EXAMPLE 5

2-Bromo-3,3,3-trifluoropropanoic acid 3,3,3-Trifluoroalanine (88 g.) is dissolved in a mixture of potassium bromide (250 g.) and 2.5 N sulfuric acid (1.240 ml.). The solution is chilled to 0° C. with an ice-salt bath and sodium nitrite (65.5 g.) is added in small portions over a one hour period with vigorous stirring. The reaction mixture is stirred in the cooling bath for another hour and then extracted with ether. The organic layer is washed with water, dried over magnesium sulfate and concentrated to dryness in vacuo to yield 2-bromo-3,3,3-trifluoropropanoic acid.

EXAMPLE 6

2-Bromo-3,3,3-trifluoropropanoic acid chloride

A solution of 2-bromo-3,3,3-trifluoropropanoic acid (5 g.) in thionyl chloride (5 ml.) is refluxed in the steam bath for two hours. The excess thionyl chloride is removed in vacuo, and the residue distilled under reduced pressure to yield 2-bromo-3,3,3-trifluoropropanoic acid chloride.

EXAMPLE 7

1-(2-Acetylthio-3,3,3-trifluoropropanoyl)-L-proline

To a solution of L-proline (5.75 g.) in 1 N sodium hydroxide (50 ml), chilled in an ice-water bath, 2-bromo-3,3,3-trifluoropropanoic acid chloride (12 g.) is added and the mixture is vigorously stirred at room temperature for three hours. A solution of thiolacetic acid (4 ml.) and potassium carbonate (4.8 g.) in water (50 ml.) is added and the mixture is stirred at room temperature for sixteen hours. After extraction with ethyl acetate, the aqueous layer is acidified with concentrated hydrochloric acid and extracted again with ethyl acetate. This last organic phase is dried over magnesium sulfate and concentrated to dryness in vacuo. The residue is chromatographed on a silica gel column with a mixture of benzeneacetic acid (7:2) to yield 1-(2-acetylthio-3,3,3-trifluoropropanoyl)-L-proline.

EXAMPLE 8

1-(2-Mercapto-3,3,3-trifluoropropanoyl)-L-proline 1-(2-Acetylthio-3,3,3-trifluoropropanoyl)-L-proline (4 g.) is dissolved in a mixture of water (8 ml.) and concentrated ammonia (8 ml.) under a blanket of nitrogen. After thirty minutes at room temperature, the reaction mixture is acidified and extracted with ethyl acetate. The organic phase is dried over magnesium sulfate and concentrated to dryness in vacuo to yield 1-(2-mercapto-3,3,3-trifluoropropanoyl)-L-proline.

EXAMPLE 9

1,1'-[Dithiobis-(2-trifluoromethyl-3-propanoyl)]-bis-L-proline 1-(3-Mercapto-2-trifluoromethylpropanoyl)-L-proline (1 g.) is dissolved in water adjusted to pH 7 with N sodium hydroxide. An ethanolic solution of iodine is added dropwise while maintaining the pH between 6 and 7 by careful addition of N sodium hydroxide. When a permanent yellow color is obtained, the addition of iodine is stopped and the color is discharged with sodium thiosulfate. The reaction mixture is acidified and extracted with ethyl acetate. The organic layer is dried over magnesium sulfate and concentrated to dryness to yield 1,1'-[dithiobis-(2-trifluoromethyl-3-propanoyl)]-bis-L-proline.

EXAMPLE 10

1-(3-Acetylthio-2-trifluoromethylpropanoyl)-L-proline sodium salt

A suspension of 1-(3-acetylthio-2-trifluoromethylpropanoyl)-L-proline (1 g.) in water (10 ml.) is adjusted to pH 8 by addition of normal sodium hydroxide. The resulting solution is freeze dried to yield 1-(3-acetylthio-2-trifluoromethylpropanoyl)-L-proline sodium salt.

EXAMPLE 11

1-(3-Acetylthio-2-trifluoromethylpropanoyl)-4,4-difluoro-L-proline

To a solution of 4,4-difluoro-2-proline (7.5 g.) in N sodium hydroxide (50 ml.) chilled in an ice-water bath, 3-acetylthio-2-trifluoromethylpropanoic acid chloride (prepared from 3-acetylthio-2-trifluoromethylpropanoic acid and thionyl chloride by the procedure of Example 6,) (12 g.) is added and the mixture is vigorously stirred at room temperature for two hours. After acidification with concentrated hydrochloric acid, the aqueous mixture is extracted with ethyl acetate. The organic phase is dried over magnesium sulfate and concentrated to dryness to yield 1-(3-acetylthio-2-trifluoromethylpropanoyl)-4,4-difluoro-L-proline.

EXAMPLE 12

1-(3-Mercapto-2-trifluoromethylpropanoyl)-4,4-difluoro-L-proline

By substituting 1-(3-acetylthio-2-trifluoromethylpropanoyl)-4,4-difluoro-L-proline for the 1-(3-acetylthio-2-trifluoromethylpropanoyl)-L-proline in the procedure of Example 4, 1-(3-mercapto-2-trifluoromethylpropanoyl)-4,4-difluoro-L-proline is obtained.

EXAMPLE 13

1,1'-[Dithiobis-(2-trifluoromethyl-3-propanoyl)]-bis-4,4-difluoro-L-proline

By substituting 1-(3-mercapto-2-trifluoromethylpropanoyl)-4,4-difluoro-L-proline for the 1-(3-mercapto-2-trifluoromethylpropanoyl)-L-proline in the procedure of Example 9, 1,1'-[dithiobis-(2-trifluoromethyl-3-propanoyl)]-bis-4,4-difluoro-L-proline is obtained.

EXAMPLE 14

1-(4,4,4-Trifluoro-2-butenoyl)-L-proline

Boric anhydride (7.0 g., 0.1 mole) (prepared by fusing boric acid in a platinum crucible and crushing under nitrogen) is combined with ethyl 3-hydroxy-4,4,4-trifluorobutanoate (32.2 g., 0.173 mole) in a 50 ml. flask equipped with a Dean-Stark trap and the mixture is heated at 180° with a salt bath until all of the anhydride dissolves (6 hours). The heat is increased to 350° during which time 23 ml. of distillate accumulates in the trap. The distillate is returned to the reaction flask and the heating step is repeated. This process is repeated 4 times to assure complete dehydration of the hydroxy ester. The distillate is dissolved in petroleum ether, dried over phosphorous pentoxide and distilled, yielding 10 g. of 4,4,4-trifluoro-2-butenoic acid ethyl ester (b.p. 115°–120°) and 650 mg. of 4,4,4-trifluoro-2-butenoic acid (b.p. 150°, 53°–55° recrystallization from pentane).

The ester is combined with 10% aqueous sodium hydroxide (24 ml.) and stirred at 25° for 6 hours. The mixture is diluted with water and extracted with methylene chloride to remove unchanged material. The aqueous layer is adjusted to pH 3 with concentrated hydrochloric acid and this mixture is extracted with methylene chloride (3×50 ml.). The organic layers are combined, dried over sodium sulfate, concentrated and the residue distilled giving crystalline 4,4,4-trifluoro-2-butenoic acid (b.p. 145°–153°). Recrystallized from pentane, the acid melts at 54°–55°, yield 4.6 g.

A mixture of the 4,4,4-trifluoro-2-butenoic acid (4.91 g., 35 mmole), hydroxybenzotriazole (4.73 g., 35 mmole), L-proline-t-butyl ester (6.00 g., 35 mmole) and dicyclohexylcarbodiimide (7.22 g., 35 mmole) in methylene chloride (200 ml.) is stirred under nitrogen overnight at room temperature. The mixture is filtered, the filtrate washed with 5% sodium bisulfate (2×50 ml.) and saturated sodium bicarbonate (2×50 ml.), dried over sodium sulfate and concentrated to yield an oil. This is dissolved in ether and the solution is chilled and filtered free of precipitate. The filtrate is concentrated, yielding a solid (m.p. 95°–100°, 8.7 g.) which shows a single spot by TLC (silica gel EM 50/50, EtOAc/$CH_2Cl_2$, Rf=0.85).

A mixture of the above obtained 1-(4,4,4-trifluoro-2-butenoyl)-L-proline t-butyl ester (4.0 g., 13.6 mmole) is mixed with trifluoroacetic acid (60 ml.) and anisole (13 ml.) and stirred under nitrogen for one hour. The solvents are removed under vacuum and the residue, dissolved in ether (10 ml.), is poured into pentane (500 ml.). This precipitation technique is repeated and the residue allowed to stand at 0° for 72 hours during which time crystallization occurs. The 1-(4,4,4-trifluoro-2-butenoyl)-L-proline is recrystallized from ethyl acetate-hexane; yield 2.48 g., m.p. 119°–120°.

EXAMPLE 15

1-(3-Mercapto-4,4,4-trifluorobutanoyl)-L-proline

Thiolacetic acid (1.5 ml.) is combined with 1-(4,4,4-trifluoro-2-butenoyl)-L-proline (720 mg., 3 mmole) under argon and the mixture stirred at room temperature overnight. The excess thiolacetic acid is removed under vacuum and the residual 1-(3-acetylthio-4,4,4-trifluorobutanoyl)-L-proline is mixed with aqueous ammonia (15 ml. conc. $NH_3$+15 ml. water) and stirred for 2 hours at room temperature. The mixture is then diluted with ice and acidified with concentrated hydrochloric acid. The acid mixture is extracted with methylene chloride (3×50 ml.), the extracts dried over sodium sulfate and concentrated to yield an oil. This is purified by dissolving in water (double distilled), treating the solution with carbon and filtering through a millipore filter (0.4 μm followed by 0.08 μm). Lyophilization of this solution gives 700 mg. of 1-(3-mercapto- 4,4,4-trifluorobutanoyl)-L-proline as a colorless glass. Rf (benzene:acetic acid 7:1) 0.24.

EXAMPLE 16

3-Acetylthio-4,4,4-trifluorobutanoic acid chloride

By substituting 4,4,4-trifluoro-2-butenoic acid for the 2-trifluoromethyl acrylic acid in the procedure of Example 1, 3-acetylthio-4,4,4-trifluorobutanoic acid is obtained, then chlorinating with thionyl chloride as in Example 6, 3-acetylthio-4,4,4-trifluorobutanoic acid chloride is obtained.

EXAMPLE 17

1-(3-Mercapto-4,4,4-trifluorobutanoyl)-4,4-difluoro-L-proline

By substituting 1-(3-acetylthio-4,4,4-trifluorobutanoic acid chloride for the 3-acetylthio-2-trifluoromethylpropanoic acid chloride in the procedure of Example 11 and then submitting the product to the procedure of Example 4, 1-(3-mercapto-4,4,4-trifluorobutanoyl)-4,4-difluoro-L-proline is obtained.

EXAMPLE 18

1,1'-[Dithiobis-(4,4,4-trifluoro-3-butanoyl)]-bis-L-proline

By substituting 1-(3-mercapto-4,4,4-trifluorobutanoyl)-L-proline for the 1-(3-mercapto-2-trifluoromethylpropanoyl)-L-proline in the procedure of Example 9, 1,1'-[dithiobis-(4,4,4-trifluoro-3-butanoyl)]-bis-L-proline is obtained.

EXAMPLE 19 cis-4-Fluoro-L-proline, hydrobromide (a) N-Carbobenzyloxy-4-hydroxy-L-proline, methyl ester N-Carbobenzyloxy-4-hydroxy-L-proline [12.4 g. (0.047 mole)] is esterified with diazomethane in dioxane-ether as described in JACS, 79, 191 (1957). To avoid freezing of the dioxane the addition of the diazomethane solution is begun at 10° and completed at 0°-2°. The yield of nearly colorless viscous oil is 14.6 g. (100%).

(b) N-Carbobenzyloxy-4-tosyloxy-L-proline, methyl ester

A stirred solution of 14.5 g. (0.052 mole) of N-carbobenzyloxy-4-hydroxy-L-proline, methyl ester in 30 ml. of pyridine is treated dropwise at −5° to −8° with a solution of 11 g. (0.058 mole) of tosyl chloride in 15 ml. of pyridine. The pale yellow solution is stored in the cold for 3 days, then added with stirring to 300 ml. of ice-cold 2 N hydrochloric acid. The precipitated gum is extracted with 200 ml. of chloroform. The aqueous phase is extracted with additional chloroform (3×100 ml.). The organic layers are combined, dried (MgSO4), and the solvent evaporated to give a pale yellow viscous oil. The oil is dissolved in 100 ml. of methanol and diluted to 400 ml. with water to precipitate the product as an oil which gradually crystallizes on seeding, rubbing, and cooling: yield 17.4 g. (77%); m.p. 62°-65°. Following crystallization from 85 ml. of isopropanol, the colorless solid N-carbobenzyloxy-4-tosyloxy-L-proline, methyl ester weighs 15.9 g. (70%); m.p. 67°-69°; $[\alpha]_D^{26} -30°$ (c=1; methanol).

(c) cis-N-Carbobenzyloxy-4-fluoro-L-proline, methyl ester

A stirred suspension of 19.1 g. (0.044 mole) of N-carbobenzyloxy-4-tosyloxy-L-proline, methyl ester in 100 ml. of redistilled diethylene glycol is treated at 42° (under argon) with 19.1 g. (0.33 mole) of anhydrous potassium fluoride and the resulting solution is heated at 81°-84° for 20 hours. After cooling, the light yellow solution is worked up to give 18.6 g. (100%) of cis-N-carbobenzyloxy-4-fluoro-L-proline, methyl ester as a light yellow oil.

(d) cis-N-Carbobenzyloxy-4-fluoro-L-proline

The cis-N-carbobenzyloxy-4-fluoro-L-proline, methyl ester (18.4 g., approximately 0.044 mole) is dissolved in 140 ml. of methanol, treated dropwise at −1° to 4° with 33 ml. (0.066 mole) of 2 N sodium hydroxide, then kept at 0° for one hour, and at room temperature overnight. After removing about ½ of the solvent on a rotary evaporator, the solution is diluted with 300 ml. of water, washed with ether (wash discarded), acidified while cooling with 12.5 ml. of 1:1 hydrochloric acid to pH 2, and extracted with ethyl acetate (4×150 ml.). The extracts are combined, washed with 100 ml. of saturated sodium chloride solution, dried (MgSO4) and the solvent evaporated to give 13.8 g. of a pale yellow viscous oil. The latter is dissolved in 60 ml. of ethanol, treated with 5.1 g. of cyclohexylamine in 10 ml. of ethanol and diluted to 900 ml. with ether. On seeding and rubbing, crystalline cis-N-carbobenzyloxy-4-fluoro-L-proline, cyclohexylamine salt separates: weight after cooling overnight, 11.0 g., m.p. 180°-183° (s. 175°). Following crystallization from 70 ml. of ethanol, the colorless solid weighs 7.6 g., m.p. 185°-187°, $[\alpha]_D^{25} -40°$ (c=1; methanol).

The cyclohexylamine salt is suspended in 75 ml. of ethyl acetate, stirred, and treated with 45 ml. of hydrochloric acid. The layers are separated, the aqueous phase is extracted with additional ethyl acetate (2×75 ml.), then the combined organic layers are dried (MgSO4), and the solvent evaporated. The residual free acid, cis-N-carbobenzyloxy-4-fluoro-L-proline crystallizes when finally dried at 0.2 mm. and 45°; yield 5.7 g. (49%); m.p. 116°-118°.

(e) cis-4-Fluoro-L-proline, hydrobromide

The cis-N-carbobenzyloxy-4-fluoro-L-proline (5.5 g., 0.021 mole) is treated with 28 ml. of hydrogen bromide in acetic acid (30-32%), stoppered loosely, and stirred for one hour. Ether (300 ml.) is added to the yellow mixture and when the crystalline product has settled the ethereal liquor is decanted and the material washed with 300 ml. of fresh ether by decantation. The product is finally heated in the steam-bath with 70 ml. of methyl ethyl ketone, cooled for two hours, washed with cold methyl ethyl ketone and with ether, and dried in vacuo. The yield of nearly colorless solid, cis-4-fluoro-L-proline, hydrobromide is 3.8 g. (86%), m.p. 189°-191° (dec.), $[\alpha]_D^{26} -19°$ (c=1, methanol).

A portion of the crude hydrobromide salt is converted to the free acid by passing through a column of Dowex 1-X8 ion exchange resin.

EXAMPLE 20 cis-1-[D-3-(acetylthio)-2-methylpropanoyl]-4-fluoro-L-proline cis-4-Fluoro-L-proline, hydrobromide (4.5 g., 0.021 mole), and 4.2 g. (0.023 mole) of D-3-acetylthio-2-methylpropanoic acid chloride are reacted in 50 ml. of water in the presence of sodium carbonate to stabilize the pH at 8.0–8.2 during the acylation (approximately 20 minutes). The mixture is worked up after an additional hour by washing with ethyl acetate (2×50 ml.), layering over with ethyl acetate, acidifying with hydrochloric acid to pH 2, saturating with sodium chloride and then separating the layers. The aqueous phase is extracted with additional ethyl acetate and the organic layers are combined, dried and evaporated. The solid residue from the ethyl acetate evaporation is rubbed under ether and the evaporation repeated; weight of colorless product, 5.4 g. (93%), m.p. 146°–148° (s. 133°) $[\alpha]_D^{26} - 132°$ (c=1; methanol). The dicyclohexylamine salt is prepared by adding dicyclohexylamine to the cis-1-[D-3-(acetylthio)-2-methylpropanoyl]-4-fluoro-L-proline in 70 ml. of ethyl acetate. 8.1 gm. of salt, which crystallizes out, are obtained, m.p. 202°–204° (s. 187°); $[\alpha]_D^{26} - 72°$ (c=1; methanol). Crystallization from 90 ml. of isopropanol gives 7.0 g., m.p. 205°–207° (s, 190°). $[\alpha]_D^{26} - 74°$. A sample recrystallized from ethanol shows no further change in m.p. or $[\alpha]_D$.

The dicyclohexylamine salt (16.9 g.) is converted back to the free acid by distribution between 10% potassium bisulfate and ethyl acetate (60 ml. 10% KHSO$_4$; 4×50 ml. ethyl acetate extractions). The organic layers are combined and evaporated to dryness to obtain 4.1 g. (71%) of colorless free acid, m.p. 154°–156° (s. 140°), $[\alpha]_D^{26} - 142°$ (c=1; methanol).

EXAMPLE 21 cis-4-Fluoro-1-(D-3-mercapto-2-methylpropanoyl)-L-proline cis-1-[D-3-(Acetylthio)-2-methylpropanoyl]-4-fluoro-L-proline (3.9 g., 0.014 mole) is hydrolyzed in 22 ml. of water containing 9 ml. of concentrated ammonium hydroxide. The reaction mixture is acidified with hydrochloric acid and extracted with ethyl acetate. The organic layer is concentrated to dryness to give 3.3 g. of glass-like product which slowly crystallizes when dried at 0.2 mm. and 50°. The material is triturated with 20 ml. of ethyl acetate (with slight warming under argon), diluted with 25 ml. of hexane, rubbed, and cooled overnight (under argon). Following filtration under argon, washing with hexane, and drying in vacuo, the colorless solid cis-4-fluoro-1-(D-3-mercapto-2-methylpropanoyl)-L-proline weighs 2.8 g. (85%), m.p. 135°–137° (s. 129°), $[\alpha]_D^{26} - 116°$ (c=1; methanol).

EXAMPLE 22

1-[3-(Acetylthio)-2-chloropropanoyl]-L-proline (Isomer A)

L-Proline (1.44 g.) and sodium carbonate (667 mg.) are dissolved in 17 ml. of water and stirred in an ice bath. To this sodium carbonate (2 g.) in 8.5 mg. of water is added, followed immediately by 3-acetylthio-2-chloropropanoic acid chloride (2.5 g.). The ice bath is removed. After 30 minutes a precipitate forms which is solubilized with the addition of 17 ml. of water. After a total of 1.5 hours, the reaction mixture is extracted twice with ethyl acetate. The aqueous layer is chilled, acidified with concentrated hydrochloric acid, saturated with sodium chloride, extracted into ethyl acetate, dried over magnesium sulfate and concentrated to dryness in vacuo to obtain the product as a crude oil, yield 3.3 g.

The oil is applied to a 100 g. silica gel column and eluted with benzene/acetic acid 7:1 to yield 2 g. of product which is crystallized from water to yield 450 mg. of 1-[3-(acetylthio)-2-chloropropanoyl]-L-proline, m.p. 111°–113°. $[\alpha]_D - 170°$ (c=1; methanol)

EXAMPLE 23

1-[3-(Acetylthio)-2-chloropropanoyl]-L-proline (Isomer B)

The aqueous mother liquors from Example 22 are lyophilized and chromatographed on silica gel with benzene/acetic acid 7:1. The fractions containing the UV absorbing material and shown to be homogeneous by TLC are pooled, concentrated to dryness and crystallized from water, yield 800 mg., m.p. 90°–109° $[\alpha]_D^{25} - 4°$ (c=2.1; ethanol). The mother liquors are concentrated to dryness by freeze-drying and the residual 1-[3-(acetylthio)-2-chloropropanoyl]-L-proline, (Isomer B) is crystallized from etherhexane; yield 380 mg., m.p. 108°–110°, $[\alpha]_D^{25} + 17.6°$ (c=1.25; ethanol).

EXAMPLE 24

1-[3-(Acetylthio)-2-bromopropanoyl]-L-proline

By substituting 3-acetylthio-2-bromopropanoic acid chloride for the 3-acetylthio-2-chloropropanoic acid chloride in the procedure of Example 22, 1-[3-(acetylthio)-2-bromopropanoyl]-L-proline is obtained, m.p. 109°–110°, $[\alpha]_D - 162°$ (c=1.39; ethanol).

EXAMPLE 25 cis-4-Chloro-1-(D-3-mercapto-2-methylpropanoyl)-L-proline (a) N-Tosyl-cis-4-chloro-L-proline, methyl ester A stirred solution of 7.9 g. (0.026 mole) of N-tosyl-cis-4-hydroxy-L-proline, methyl ester in 80 ml. of chloroform is treated portionwise with 11.9 g. (0.057 mole) of phosphorous pentachloride. The temperature rises gradually to 40° accompanied by foaming. When the foaming ceases and the temperature begins to drop, the mixture is refluxed for 0.5 hours, cooled, and worked up as described in Aust. J. Chem. 20, 1500–1502. The almost completely solid residue (11.6 g.) is crystallized from 40 ml. of warm benzene—80 ml. of hexane to yield 6.8 g. of colorless N-tosyl-cis-4-chloro-L-proline, methyl ester; m.p. 88°–90° (s. 82°); $[\alpha]_D^{25} - 44°$ (c=1.5, chloroform).

(b) N-Tosyl-cis-4-chloro-L-proline

The ester product (6.7 g., 0.021 mole) from part (a) is saponified in 50 ml. of methanol with 23 ml. of 1 N sodium hydroxide (stirring overnight) to yield 4.8 g. of N-tosyl-cis-4-chloro-L-proline; m.p. 172°–174° (s. 165°); $[\alpha]_D^{25} - 50°$ (c=2, ethanol).

(c) cis-4-Chloro-L-proline, hydrobromide

The product (2.3 g., 0.0076 mole) from part (b) is treated with 17 ml. of 30–32% hydrogen bromide in acetic acid in the presence of 1.6 g. (0.017 mole) of phenol according to the procedure described in Aust. J. Chem., 20, 1500–1502 to yield 1.75 g. of nearly colorless cis-4-chloro-L-proline, hydrobromide; m.p. 204°-206° (dec.).

(d)
cis-1-[D-3-(Acetylthio)-2-methylpropanoyl]-4-chloro-L-proline cis-4-Chloro-L-proline, hydrobromide (3.15 g., 0.0137 mole) and 2.8 g. (0.015 mole) of D-3-acetylthio-2-methylpropanoic acid chloride dissolved in 4 ml. of ether are reacted in 40 ml. of water in the presence of sodium carbonate as set forth in Example 20. Initially, 2.3 g. of sodium carbonate is required to stabilize the pH at 8.2 and during the acylation approximately 8 ml. of 25% sodium carbonate (w/v) is consumed in stabilizing the pH at 8.2-8.4 (approximately 10 minutes). The mixture is worked up after an additional hour to give 3.6 g. of a viscous oil.

The dicyclohexylamine salt is prepared by adding dicyclohexylamine to the cis-1-[D-3-(acetylthio)-2-methylpropanoyl]-4-chloro-L-proline in 55 ml. of ethyl acetate. 3.2 g. of salt, which crystallizes out, are obtained m.p. 189°-192° (s. 185°); $[\alpha]_D^{26} -49°$ (c=1; ethanol). Crystallization from 20 ml. of isopropanol gives 2.6 g., m.p. 190°-192° (s=188°); $[\alpha]_D^{25} -50°$.

This dicyclohexylamine salt (2.5 g.) is converted back to the free acid by distribution between 10% potassium bisulfate and ethyl acetate (25 ml. 10% KHSO$_4$; 4×25 ml. ethyl acetate extractions) to yield 1.6 g. of cis-1-[D-3(acetylthio)-2-methylpropanoyl]-4-chloro-L-proline which crystallizes slowly on standing.

(e)
cis-4-Chloro-1-(D-3-mercapto-2-methylpropanoyl)-L-proline cis-1-[D-3-(Acetylthio)-2-methylpropanoyl]-4-chloro-L-proline (1.6 g., 0.0054 mole) is hydrolyzed in 9 ml. of water containing 4 ml. of concentrated ammonium hydroxide as described in Example 21. The reaction mixture is acidified with 7 ml. of 1:1 hydrochloric acid to give 1.2 g. of product which begins to crystallize when dried at 0.2 mm. The material is rubbed under 7 ml. of ethyl acetate, diluted with 15 ml. of hexane, and cooled overnight (under argon). Following filtration under argon, washing with hexane, and drying in vacuo, the colorless solid cis-4-chloro-1-(D-3-mercapto-2-methylpropanoyl)-L-proline weighs 1.1 g. (80%); m.p. 138°-140° (s. 134°); $[\alpha]_D^{26} -79°$ (c=1; ethanol).

EXAMPLE 26 trans-4-Bromo-1-(D-3-mercapto-2-methylpropanoyl)-L-proline

By substituting trans-4-bromo-L-proline [Aust. J. Chem. 20, 1493 (1967)] for the cis-4-fluoro-L-proline hydrobromide in the procedure of Example 20, and then submitting the product to the procedure of Example 21, trans-1-[D-3-(acetylthio)-2-methylpropanoyl]-4-bromo-L-proline and trans-4-bromo-1-(D-3-mercapto-2-methylpropanoyl)-L-proline are obtained.

EXAMPLE 27 cis-4-Iodo-1-(D-3-mercapto-2-methylpropanoyl)-L-proline

By substituting cis-4-iodo-L-proline for the cis-4-fluoro-L-proline hydrobromide in the procedure of Example 20, and then submitting the product to the procedure of Example 21, cis-1-[D-3-(acetylthio)-2-methylpropanoyl]-4-iodo-L-proline, and cis-4-iodo-1-[D-3-mercapto-2-methylpropanoyl]-L-proline are obtained.

EXAMPLE 28

4,4-Difluoro-1-(D-3-mercapto-2-methylpropanoyl)-L-proline (a) N-Carbobenzyloxy-4,4-difluoro-L-proline, methyl ester To a cooled stirred solution of 3.3 grams of N-carbobenzyloxy-4-keto-L-proline, methyl ester in 80 ml. of methylene dichloride there is added dropwise 3.3 ml. diethylaminosulfurtrifluoride. The reaction mixture is allowed to remain overnight at room temperature. About 100 grams of crushed ice is added with stirring and the reaction mixture stirred for 45 minutes. The organic layer is separated and the aqueous layer extracted with methylene chloride (2×40 ml.). The combined extracts are dried over anhydrous magnesium sulfate and then concentrated under reduced pressure to yield the desired N-carbobenzyloxy-4,4-difluoro-L-proline, methyl ester.

(b) N-carbobenzyloxy-4,4-difluoro-L-proline

A solution of 5.6 grams of N-carbobenzyloxy-4,4-difluoro-L-proline, methyl ester in 50 ml. of methanol is treated dropwise with 11.5 ml. of 2 N sodium hydroxide solution at 0°-5°. The reaction mixture is left at 0° for 1 hour and is then allowed to warm to room temperature overnight. The reaction mixture is concentrated under reduced pressure to about one-half its original volume and is then diluted with 100 ml. of water. The aqueous reaction mixture is extracted with ether and the ether extracts discarded. The aqueous solution is acidified with cooling with dilute hydrochloric acid to pH 2 and is then extracted with ethyl acetate (3×50 ml.). The ethyl acetate extracts are combined and washed with saturated sodium chloride solution, dried over anhydrous magnesium sulfate and concentrated to yield the desired product, N-carbobenzyloxy-4,4-difluoro-L-proline. It is purified by conversion to the cyclohexylamine salt, m.p. 180°-185° $[\alpha]_D^{26} -24°$ (c=1%; ethanol).

The free acid is obtained by treating an aqueous solution of the cyclohexylamine salt with hydrochloric acid and extracting the mixture with ethyl acetate (4×30 ml.). The ethyl acetate extracts are dried over anhydrous magnesium sulfate and concentrated under reduced pressure to yield the desired N-carbobenzyloxy-4,4-difluoro-L-proline.

(c) 4,4-Difluoro-L-proline, hydrobromide

A mixture of 2.4 grams of N-carbobenzyloxy-4,4-difluoro-L-proline and 12 ml. of hydrogen bromide in acetic acid (30-32%) is stirred for 30 minutes at room temperature and then 300 ml. of anhydrous ether is added. The mixture is cooled and the precipitated solid is filtered and dried under reduced pressure. The desired 4,4-difluoro-L-proline, hydrobromide melts at 163°-165° (s. 160°); $[\alpha]_D^{26} -14°$ (c=1%; methanol).

(d)
1-[D-3-(Acetylthio)-2-methylpropanoyl]-4,4-difluoro-L-proline 4,4-Difluoro-L-proline, hydrobromide (2.7 g., 0.0116 mole) and 2.4 g. (0.013 mole) of D-3-acetylthio-2-methylpropanoic chloride dissolved in 3 ml. of ether are reacted with continued stirring and cooling in 30 ml. of water and in the presence of sodium carbonate as set forth in Example 20. Approximately 17 ml. of 25% sodium carbonate (w/v) is required to bring the pH initially to 8.4 and to maintain it at 7.5-8.3 during the acylation. The stirring and cooling is continued for one hour after the addition is completed. The reaction mixture is extracted with ethyl acetate (2×25 ml.) and the extracts discarded. To the aqueous layer is added 50 ml. of ethyl acetate and, with stirring and cooling, there is added dropwise concentrated hydrochloric acid to a pH of 2.0. The aqueous layer is saturated with sodium chloride and the ethyl acetate layer separated. The aqueous layer is extracted with ethyl acetate (3×25 ml.) and the combined ethyl acetate extracts dried over anhydrous magnesium sulfate and concentrated under reduced pressure to yield the desired product in crude form as a yellow viscous oil.

The dicyclohexylamine amine salt is prepared by adding 2.3 g. of dicyclohexylamine to 3.5 g. of the 1-[D-3-(acetylthio)-2-methylpropanoyl]-4,4-difluoro-L-proline in 45 ml. of ethyl acetate. 4.1 g. of salt, which crystallize out are obtained, m.p. 217°–219° (s. 205°); $[\alpha]_D^{26} -64°$ (c=1; methanol). Recrystallization from 45 ml. of ethanol gives 3.3 g. of colorless solid, m.p. 225°–227° (s. 215°); $[\alpha]_D^{26} -70°$ (c=1; methanol).

The dicyclohexylamine salt is converted back to the free acid by distribution between 10% potassium bisulfate and ethyl acetate (30 ml. of 10% KHSO$_4$; 4×30 ml. ethyl acetate extractions) to yield 1-[D-3-(acetylthio)-2-methylpropanoyl]-4,4-difluoro-2-proline as a nearly colorless syrup.

(e)
4,4-Difluoro-1-(D-3-mercapto-2-methylpropanoyl)-L-proline

1-[D-3-(Acetylthio)-2-methylpropanoyl]-4,4-difluoro-L-proline (2.1 g., 0.071 mole) is hydrolyzed in 11 ml. of water containing 4.6 ml. of concentrated ammonium hydroxide according to the procedure of Example 21 to yield 1.8 g. of 4,4-difluoro-1-(D-3-mercapto-2-methylpropanoyl)-L-proline as a nearly colorless, viscous, syrupy product; $[\alpha]_D^{26} -85°$ (c=1, methanol).

Calculated for $C_9H_{13}F_2NO_3S$: C, 42.68; H, 5.17; N, 5.53; S, 12.66. Found: C, 42.59; H, 5.49; N, 5.62; S, 12.41.

EXAMPLE 29 cis-3-Fluoro-DL-proline, hydrobromide

By substituting N-carbobenzyloxy-3-hydroxy-DL-proline [J. Am. Chem. Soc. 85, 2824 (1963)] for the N-carbobenzyloxy-4-hydroxy-L-proline in the procedure of Example 19, cis-3-fluoro-DL-proline hydrobromide is obtained.

EXAMPLE 30 cis-3-Fluoro-1-(D-3-mercapto-2-methylpropanoyl)-DL-proline

By substituting cis-3-fluoro-DL-proline hydrobromide for the cis-4-fluoro-L-proline in the procedure of Example 20 and then submitting the product to the procedure of Example 21, cis-1-[D-3-(acetylthio)-2-methylpropanoyl]-3-fluoro-DL-proline and cis-3-fluoro-1-(D-3-mercapto-2-methylpropanoyl)-DL-proline are obtained.

EXAMPLE 31 cis-3-Chloro-1-(D-3-mercapto-2-methylpropanoyl-L-proline

By substituting cis-3-chloro-L-proline [obtained from 3-hydroxyproline by the procedure described in Aust. J. Chem. 20, 1493 (1967)] for the cis-4-fluoro-L-proline hydrobromide in the procedure of Example 20 and then submitting the product to the procedure of Example 21, cis-1-[D-3-(acetylthio)-2-methylpropanoyl]-3-chloro-L-proline, and cis-3-chloro-1-(D-3-mercapto-2-methylpropanoyl)-L-proline are obtained.

EXAMPLE 32

4,4-Dichloro-1-(D-3-mercapto-2-methylpropanoyl)-L-proline

By substituting 4,4-dichloro-L-proline [prepared from 4-keto-L-proline diketopiperazine and phosphorus pentachloride by the procedure described in J. Med. Chem. 20, 1176 (1977)] for the cis-4-fluoro-L-proline hydrobromide in the procedure of Example 20, and then submitting the product to the procedure of Example 21, 1-[D-3-(acetylthio)-2-methylpropanoyl]-4, 4-dichloro-L-proline and 4,4-dichloro-1-(D-3-mercapto-2-methylpropanoyl)-L-proline are obtained.

EXAMPLE 33

1,1'-[Dithiobis-(2-D-methylpropanoyl)]-bis-[(cis-4-fluoro)-L-proline]

By substituting cis-4-fluoro-1-(D-3-mercapto-2-methylpropanoyl)-L-proline for the 1-(3-mercapto-2-trifluoromethylpropanoyl)-L-proline in the procedure of Example 9, 1,1'-[dithiobis-(2-D-methylpropanoyl)]-bis-[(cis-4-fluoro)-L-proline] is obtained.

EXAMPLE 34

4,4-Difluoro-1-(3-mercaptobutanoyl)-L-proline

By substituting 3-acetylthiobutanoic acid chloride for the 3-acetylthio-2-trifluoromethylpropanoic acid chloride in the procedure of Example 11 and then submitting the product to the procedure of Example 12, 1-(3-acetylthiobutanoyl)-4,4-difluoro-L-proline and 4,4-difluoro-1-(3-mercaptobutanoyl)-L-proline are obtained.

EXAMPLE 35

1-(3-Propanoylthio-2-trifluoromethylpropanoyl)-L-proline

By substituting thiopropanoic acid for the thioacetic acid in the procedure of Example 1 and then submitting the product to the procedures of Examples 2 and 3, 3-propanoylthio-2-trifluoromethylpropanoic acid, 1-(3-propanoylthio-2-trifluoromethylpropanoyl)-L-proline tert butyl ester and 1-(3-propanoylthio-2-trifluoromethylpropanoyl)-L-proline, respectively, are obtained.

EXAMPLE 36

3-(4-Methoxybenzyl)thio-2-trifluoromethylpropanoic acid

A neat mixture of 1-trifluoromethylacrylic acid (3.9 g.) and 4-methoxybenzylthiol (4.3 g.) is stirred at 100°–110° for one hour. The mixture is allowed to cool to room temperature and the solid is recrystallized from cyclohexane, m.p. 72°–74°.

EXAMPLE 37

1-[3-(4-Methoxybenzyl)thio-2-trifluoromethyl-propanoyl]-L-proline tert-butyl ester A solution of 3-(4-methoxybenzyl)thio-2-trifluoromethylpropanoic acid (6.5 g.) and proline tert-butyl ester (3.76 g.) in dichloromethane (500 ml.) is stirred at 0° and treated with dicyclohexylcarbodiimide (4.53 g.) After 30 minutes at 0° and overnight at room temperature, the mixture is filtered and the filtrate is washed neutral. The organic layer is dried and concentrated to dryness in vacuo. The TLC [silica gel methylene chloride/ethyl acetate (95:5)] shows two major spots $R_f$ 0.46 and 0.51 corresponding to the two diastereoisomers.

EXAMPLE 38

1-(D,L-3-Mercapto-2-trifluoromethylpropanoyl)-L-proline

A solution of 1-[3-(4-methoxybenzyl)thio-2-trifluoromethylpropanoyl]-L-proline tert-butyl ester (4.47 g.) obtained in Example 37 and anisole (10 ml.) is cooled to 0° and trifluoroacetic acid (100 ml.) is added, followed by mercuric acetate (3.18 g.). The bath is removed and the mixture is stirred at room temperature for one hour. The mixture is concentrated to dryness in vacuo and the residue is triturated with ether-hexane. The insoluble material is suspended in water and hydrogen sulfide is bubbled through for 10 minutes. The precipitate is removed by filtration and the filtrate is freeze dried to give the product, 1-(D,L-3-mercapto-2-trifluoromethylpropanoyl)-L-proline as an amorphous solid. $R_f$ 0.29-0.31 (silica gel-benzene:acetic acid 7:1).

EXAMPLE 39

1-(3-Mercapto-2-trifluoromethylpropanoyl)-L-proline (Isomer A) and 1-(3-mercapto-2-trifluoromethylpropanoyl)-L-proline (Isomer B)

1-[3-(4-Methoxybenzyl)thio-2-trifluoromethylpropanoyl]-L-proline, tert-butyl ester (3.5 g.) from Example 37 is chromatographed on silica gel (500 g.—Baker 7 #5-3406) in a Jobin Yvon Chromatospac Prep 100 apparatus. The column is eluted with dichloromethane/ethyl acetate (96:4) to give 0.85 g. of the component having the higher $R_f$, 0.3 g. of a mixture of the two components, and 1.2 g. of the component having the lower $R_f$.

The 0.85 g. of the higher $R_f$ component is treated with anisole and mercuric acetate in trifluoroacetic acid followed by treatment with hydrogen sulfide gas, as set forth in Example 38, to yield 0.6 g. of the desired product as an oil. This material is freeze dried to give 0.514 g. of 1-(3-mercapto-2-trifluoromethylpropanoyl)-L-proline (Isomer A).

Calculated for $C_9H_{12}F_3NO_3S \cdot \frac{1}{3} H_2O$: C, 38.99; H, 4.38; N, 5.05, F, 20.55; S, 11.56. Found: C, 39.14; H, 4.07; N, 5.08; F, 20.67; S, 11.65.

The 1.2 g. of the lower $R_f$ component is also treated with anisole and mercuric acetate in trifluoroacetic acid followed by treatment with hydrogen sulfide gas, as set forth in Example 38, to give after freeze drying and trituration of the residue with pentane, 0.7 g. of desired product, m.p. 98°–110°. Recrystallization from diisopropyl ether gives 0.4 g. of 1-(3-mercapto-2-trifluoromethylpropanoyl)-L-proline (Isomer B); m.p. 105°–107°.

Calculated for $C_9H_{12}F_3NO_3S$: C, 39.48; H, 4.46; N, 5.16; F, 21.01; S, 11.82. Found: C, 40.22; H, 4.48; N, 5.01; F, 21.35; S, 11.57.

EXAMPLE 40 cis-4-Fluoro-1-(3-mercapto-2-trifluoromethyl-propanoyl)-L-proline

By substituting 3-acetylthio-2-trifluoromethylpropanoic acid chloride for the 3-acetylthio-2-methylpropanoic acid chloride in the procedure of Example 20 and then submitting the product to the procedure of Example 21, cis-1-[3-(acetylthio)-2-trifluoromethylpropanoyl]-4-fluoro-L-proline and cis-4-fluoro-1-(3-mercapto-2-trifluoromethylpropanoyl)-L-proline, respectively, are obtained.

EXAMPLE 41 trans-4-Fluoro-1-(D-3-mercapto-2-methylpropanoyl)-L-proline (a) cis-N-Carbobenzyloxy-4-hydroxy-L-proline N-Carbobenzyloxy-4-keto-L-proline (10 g., 0.038 mole) are dissolved in 300 ml. of methanol and reduced with 5.8 g. (0.15 mole) of sodium borohydride in 20 ml. of water as described in JACS, 79, 189 (1957) to give 8.7 g. of a foamy product. This material is dissolved in 30 ml. of ethanol, treated with 3.5 g. of cyclohexylamine in some ethanol, and diluted to 500 ml. with ether. On seeding and rubbing, the crystalline cyclohexylamine salt separates rapidly to give 10.8 g.; m.p. 163°–165°. This cyclohexylamine salt is then treated with 30 ml. of 2 N HCl and extracted with ethyl acetate (4×50 ml.) to yield as a glass-like material 8 g. of cis-N-carbobenzyloxy-4-hydroxy-L-proline.

(b) cis-N-Carbobenzyloxy-4-hydroxy-L-proline, methyl ester

Following the procedure of Example 19(a), 8 g. (0.03 mole) of the cis-N-carbobenzyloxy-4-hydroxy-L-proline is esterified with diazomethane to yield 9.2 g. of cis-N-carbobenzyloxy-4-hydroxy-L-proline, methyl ester as a pale yellow viscous oil.

(c) cis-N-Carbobenzyloxy-4-tosyloxy-L-proline, methyl ester

Following the procedure of Example 19(b), the methyl ester product from part (b) is treated with 12.4 g. of tosyl chloride in 45 ml. of pyridine to give 13.2 g. of cream-colored product; m.p. 114°–117° (s. 105°). 13 g. of this material are recrystallized from 70 ml. of ethanol to 8.4 g. of colorless cis-N-carbobenzyloxy-4-tosyloxy-L-proline, methyl ester; m.p. 133°–135°; $[\alpha]_D^{25} -26°$ (c=1%, chloroform).

(d) trans-N-Carbobenzyloxy-4-fluoro-L-proline, methyl ester

Following the procedure of Example 19(c), the methyl ester product (8.3 g.) from part (c) is reacted with 8.3 g. of anhydrous potassium fluoride in 85 ml. of diethylene glycol to yield 6.2 g. of trans-N-carbobenzyloxy-4-fluoro-L-proline, methyl ester.

(e) trans-N-Carbobenzyloxy-4-fluoro-L-proline

Following the procedure of Example 19(d), the methyl ester product from part (d) is saponified with 11.5 ml. of 2 N sodium hydroxide in 50 ml. methanol to give 5.3 g. of the desired product as a pale yellow viscous oil. This material is converted to the cyclohexylamine salt by treatment with 2 g. of cyclohexylamine in 25 ml. of ethanol. 4.7 g. of cyclohexylamine salt are obtained; m.p. 188°–191° (s. 183°); $[\alpha]_D^{25}$ −42° (c=1%, methanol). Crystallization from 55 ml. of isopropanol gives 3.7 g. of colorless cyclohexylamine salt; m.p. 194°–196° (s. 187°); $[\alpha]_D^{25}$ −44° (c=1%, methanol).

This cyclohexylamine salt is treated with 22 ml. of 1 N HCl and extracted with ethyl acetate (4×35 ml.) to yield 3 g. of glass-like trans-N-carbobenzyloxy-4-fluoro-L-proline.

(f) trans-4-Fluoro-L-proline, hydrobromide

Following the procedure of Example 19(e), the N-carbobenzyloxy product from part (e) is hydrolyzed with 15 ml. of hydrogen bromide in acetic acid for 1 hour to give 1.95 g. of colorless solid (triturated with 35 ml. of methyl ethyl ketone) trans-4-fluoro-L-proline, hydrobromide; m.p. 162°–164° (dec.); $[\alpha]_D^{25}$ −30° (c=1%, methanol).

(g) trans-1-[D-3-(Acetylthio)-2-methylpropanoyl]-4-fluoro-L-proline trans-4-Fluoro-L-proline, hydrobromide (1.9 g., 0.0089 mole) and 1.8 g. (0.01 mole) of D-3-acetylthio-2-methylpropanoic acid chloride dissolved (dissolved in 2.5 ml. of ether) are reacted in 25 ml. of water in the presence of sodium carbonate as described in Example 20. Initially, 1 g. of sodium carbonate is required to stabilize the pH at 8.2 and approximately 6 ml. of 25% sodium carbonate are consumed during the acylation to maintain the pH at 8.2–8.3. This reaction yields 2.6 g. of crude extremely viscous syrupy product. The dicyclohexylamine salt is prepared by adding 1.8 g. of dicyclohexylamine to the trans-1-[D-3-(acetylthio)-2-methylpropanoyl]-4-fluoro-L-proline in 35 ml. of ethyl acetate. 3.5 g. of salt, which crystallize out, are obtained; m.p. 204°–206° (s 185°); $[\alpha]_D^{26}$ −81° (C=1%, methanol). Recrystallization from 35 ml. of isopropanol gives 2.8 g. of colorless solid dicyclohexylamine salt; m.p. 209°–211° (s. 197°); $[\alpha]_D^{25}$ −85° (c=1%, methanol).

The dicyclohexylamine salt (2.75 g.) is converted back to the free acid by distribution between 10% potassium bisulfate and ethyl acetate (25 ml. of 10% KHSO₄; 4×20 ml. ethyl acetate extractions). The organic layers are combined and evaporated to dryness to obtain 1.8 g. of almost glass-like free acid.

(h) trans-4-Fluoro-1-(D-3-mercapto-2-methylpropanoyl)-L-proline trans-1-[D-3-(Acetylthio)-2-methylpropanoyl]-4-fluoro-L-proline (1.8 g., 0.0065 mole) is hydrolyzed in 10 ml. of water containing 4.2 ml. of concentrated ammonium hydroxide as set forth in Example 21. This reaction yields 1.35 g. of colorless glass-like trans-4-fluoro-1-(D-3-mercapto-2-methylpropanoyl)-L-proline; $[\alpha]_D^{26}$ −112° (c=1%, methanol).

Calculated for $C_9H_{14}FNO_3S \cdot \frac{1}{4}H_2O$: C, 45.08; H, 6.10; N, 5.84; S, 13.17. Found: C, 45.03; H, 6.14; N, 5.58; S, 12.85.

EXAMPLE 42

D-3-Acetylthio-2-methylpropanoic acid chloride

A suspension of 1-(D-3-mercapto-2-methylpropanoyl)-L-proline, (150 g., 690 mmoles), in 1274 ml. of water and 426 ml. of concentrated hydrochloric acid (5.526 moles) is refluxed under nitrogen with stirring for 8 hours. The resulting solution is kept at room temperature overnight and then extracted with 400 ml. of chloroform (10×). The combined chloroform extracts are dried over magnesium sulfate under nitrogen and then evaporated. To the residue, 81.2 g., is added acetic anhydride, (176 ml., 1.809 mole), and pyridine, 180 ml. and the mixture is kept at room temperature for 20 hours. The mixture is then evaporated and the oily residue is dissolved in 1000 ml. of ethyl acetate and the solution is washed in sequence with 200 ml. 5% hydrochloric acid-saturated sodium chloride (washing pH 2), 200 ml. of saturated sodium chloride solution (2 times, second washing pH 7) and then stripped of the solvent. To the clear oily residue, [96.9 g., 96.5%, had $[\alpha]_D^{25}$ = −61.8° (CHCl₃)] is added freshly distilled thionyl chloride, (83 ml., 1.173 mole) and the resulting solution is stirred at room temperature with evolution of gas for 18 hours. The excess thionyl chloride is evaporated under vacuum and a 50° bath and the residue is distilled at reduced pressure to obtain 56.9 g. of D-3-acetylthio-2-methylpropanoic acid chloride, b.p. 40°–44° (0.17–0.2 mmHg.). $[\alpha]_D^{25}$ −42.5° (c 2; methanol).

EXAMPLE 43

3-Acetylthio-2-chloropropanoic acid chloride

By substituting 2-chloroacrylic acid for the 2-trifluoromethylacrylic acid in the procedure of Example 1 and then allowing the product to react with thionyl chloride, 3-acetylthio-2-chloropropanoic acid and 3-acetylthio-2-chloropropanoic acid chloride are obtained.

EXAMPLE 44

3-Acetylthio-2-bromopropanoic acid chloride

By substituting 2-bromoacrylic acid for the 2-trifluoromethylacrylic acid in the procedure of Example 1 and then allowing the product to react with thionyl chloride, 3-acetylthio-2-bromopropanoic acid and 3-acetylthio-2-bromopropanoic acid chloride are obtained.

The racemic forms of the final products in each of the foregoing examples are produced by utilizing the DL-form of the starting amino acid instead of the L-form.

Similarly, the D-form of the final products in each of the foregoing examples is produced by utilizing the D-form of the starting amino acid instead of the L-form.

EXAMPLE 45

1000 tablets each containing 100 mg. of 1-(D-3-mercaptopropanoyl)-cis-4-fluoro-L-proline, are produced from the following ingredients:

| | |
|---|---|
| 1-(3-mercaptopropanoyl)-cis-4-fluoro-L-proline | 100 g. |
| Corn starch | 50 g. |
| Gelatin | 7.5 g. |
| Avicel (microcrystalline cellulose) | 25 g. |
| Magnesium stearate | 2.5 g. |

The 1-(D-3-mercaptopropanoyl)-cis-4-fluoro-L-proline and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg. of active ingredient.

EXAMPLE 46

1000 tablets each containing 200 mg. of 1-[D-3-(acetylthio)-2-methylpropanoyl]-cis-4-fluoro-L-proline are produced from the following ingredients:

| | |
|---|---|
| 1-[D-3-(acetylthio)-2-methylpropanoyl]-cis-4-fluoro-L-proline | 200 g. |
| Lactose | 100 g. |
| Avicel | 150 g. |
| Corn starch | 50 g. |
| Magnesium stearate | 5 g. |

The 1-[D-3-(acetylthio)-2-methylpropanoyl]-cis-4-fluoro-L-proline, lactose and Avicel are admixed, then blended with the corn starch. Magnesium stearate is added. The dry mixture is compressed in a tablet press to form 1000 505 mg. tablets each containing 200 mg. of active ingredient. The tablets are coated with a solution of Methocel E 15 (methyl cellulose) including as a color a lake containing yellow #6.

EXAMPLE 47

Two piece #1 gelatin capsules each containing 250 mg. of 1-(3-mercapto-4,4,4-trifluorobutanoyl)-L-proline are filled with a mixture of the following ingredients:

| | |
|---|---|
| 1-(3-mercapto-4,4,4-trifluorobutanoyl)-L-proline | 250 mg. |
| Magnesium stearate | 7 mg. |
| USP lactose | 193 mg. |

EXAMPLE 48

An injectable solution is produced as follows:

| | |
|---|---|
| cis-1-[D-3-(mercapto)-2-methylpropanoyl)]-4-fluoro-L-proline | 500 q. |
| Methyl paraben | 5 g. |
| Propyl paraben | 1 g. |
| Sodium chloride | 25 g. |
| Water for injection qs. | 5 l. |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

The products of each example can be similarly formulated as in Examples 45 to 48.

What is claimed is:

1. A compound of the formula

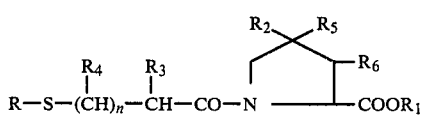

wherein
R is hydrogen, lower alkanoyl,

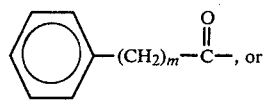

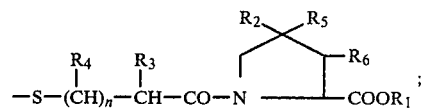

m is zero, one, or two;
$R_1$ is hydrogen or lower alkyl;
$R_2$, $R_5$ and $R_6$ each is hydrogen or halogen;
$R_3$ is hydrogen, lower alkyl, halogen or trifluoromethyl provided that when n is zero $R_3$ is other than halogen;
$R_4$ is hydrogen, lower alkyl or trifluoromethyl; and n is 0 or 1; with the provisos that at least one of $R_2$, $R_3$, $R_4$, $R_5$ and $R_6$ as defined above is a halogen and that only $R_2$ and $R_5$ can both be halogen in the same compound; and basic salts thereof.

2. A compound of the formula

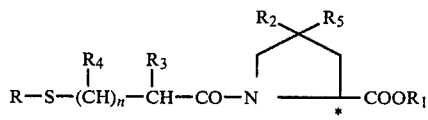

wherein
R is hydrogen, lower alkanoyl or

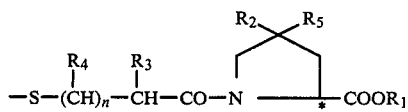

$R_1$ is hydrogen or lower alkyl;
$R_2$ and $R_5$ are each the same halogen or one is halogen and the other is hydrogen;
$R_3$ and $R_4$ each is hydrogen or trifluoromethyl, one being hydrogen and the other trifluoromethyl; and
n is 0 or 1; and physiologically acceptable salts thereof.

3. The compound of claim 2 wherein the proline as represented by the asterisk is in the L-configuration.

4. The compound of claim 3 wherein $R_2$ and $R_5$ are both fluorine.

5. The compound of claim 4 wherein R is acetyl and $R_1$ is hydrogen.

6. The compound of claim 4 wherein R and $R_1$ are both hydrogen.

7. The compound of claim 6 wherein n is one; $R_3$ is trifluoromethyl; and $R_4$ is hydrogen.

8. The compound of claim 6 wherein n is one; $R_3$ is hydrogen; and $R_4$ is trifluoromethyl.

9. The compound of claim 3 wherein $R_2$ is fluorine and $R_5$ is hydrogen.

10. The compound of claim 9 wherein R is acetyl and $R_1$ is hydrogen.

11. The compound of claim 9 wherein R and $R_1$ are both hydrogen.

12. The compound of claim 3 wherein $R_2$ is chlorine and $R_5$ is hydrogen.

13. The compound of claim 12 wherein R is acetyl and $R_1$ is hydrogen.

14. The compound of claim 12 wherein R and $R_1$ are both hydrogen.

15. A compound of the formula

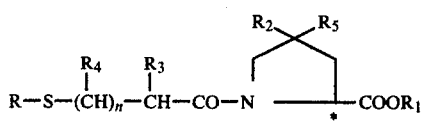

wherein

R is hydrogen, lower alkanoyl, or

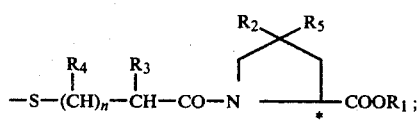

$R_1$ is hydrogen or lower alkyl;

$R_2$ and $R_5$ each is hydrogen or halogen provided that when $R_2$ and $R_5$ are both halogen the two halogens are the same;

$R_3$ is hydrogen, halogen, or lower alkyl provided that $R_3$ is halogen when $R_2$ and $R_5$ are both hydrogen and $R_3$ is other than halogen when either or both $R_2$ and $R_5$ is halogen;

$R_4$ is hydrogen; and n is zero or one provided that n is one when $R_3$ is halogen; and physiologically acceptable salts thereof.

16. The compound of claim 15 wherein the proline as represented by the asterisk is in the L-configuration.

17. The compound of claim 16 wherein $R_2$ and $R_5$ are both hydrogen; n is one; and $R_3$ is halogen.

18. The compound of claim 17 wherein $R_3$ is chlorine or bromine.

19. The compound of claim 18 wherein $R_3$ is chlorine; R is acetyl; and $R_1$ is hydrogen.

20. The compound of claim 18 wherein $R_3$ is bromine; R is acetyl; and $R_1$ is hydrogen.

21. The compound of claim 16 wherein $R_2$ and $R_5$ are both fluorine; and $R_3$ is hydrogen or methyl.

22. The compound of claim 21 wherein R and $R_1$ are both hydrogen.

23. The compound of claim 22 wherein n is one and $R_3$ is methyl.

24. The compound of claim 23, 4,4-difluoro-1-(D-3-mercapto-2-methylpropanoyl)-L-proline.

25. The compound of claim 16 wherein $R_2$ and $R_5$ are both chlorine; and $R_3$ is hydrogen or methyl.

26. The compound of claim 25 wherein R and $R_1$ are both hydrogen.

27. The compound of claim 26 wherein n is one and $R_3$ is methyl.

28. The compound of claim 16 wherein $R_2$ is fluorine; $R_5$ is hydrogen; and $R_3$ is hydrogen or methyl.

29. The compound of claim 28 wherein R and $R_1$ are both hydrogen.

30. The compound of claim 29 wherein n is one and $R_3$ is methyl.

31. The compound of claim 30, cis-4-fluoro-1-(D-3-mercapto-2-methylpropanoyl)-2-proline.

32. The compound of claim 30, trans-4-fluoro-1-(D-3-mercapto-2-methylpropanoyl)-L-proline.

33. The compound of claim 16 wherein $R_2$ is chlorine; $R_5$ is hydrogen; and $R_3$ is hydrogen or methyl.

34. The compound of claim 33 wherein R and $R_1$ are both hydrogen.

35. The compound of claim 34 wherein n is one and $R_3$ is methyl.

36. The compound of claim 35, cis-4-chloro-1-(D-3-mercapto-2-methylpropanoyl)-L-proline.

37. A method for alleviating hypertension in a hypertensive mammal which comprises administering to said mammal an effective amount of a composition comprising a compound of claim 1 or physiologically acceptable salt thereof and a pharmaceutically acceptable vehicle therefor.

38. A composition useful for alleviating hypertension in a hypertensive mammal comprising from about 10 to 500 mg. of a compound of claim 1 or physiologically acceptable salt thereof and a pharmaceutically acceptable carrier therefor.

* * * * *